(12) United States Patent
Ten Eyck et al.

(10) Patent No.: US 9,468,575 B2
(45) Date of Patent: Oct. 18, 2016

(54) SYSTEM AND METHOD OF NEONATAL CARE

(75) Inventors: Lawrence G. Ten Eyck, Ellicott City, MD (US); Steven M. Falk, Baltimore, MD (US)

(73) Assignee: General Electric Company, Schenectady, NY (US)

( * ) Notice: Subject to any disclaimer, the term of this patent is extended or adjusted under 35 U.S.C. 154(b) by 518 days.

(21) Appl. No.: 13/313,493

(22) Filed: Dec. 7, 2011

(65) Prior Publication Data

US 2013/0150655 A1 Jun. 13, 2013

(51) Int. Cl.
*A61G 11/00* (2006.01)
*A61B 5/0402* (2006.01)
*A61B 5/1455* (2006.01)

(52) U.S. Cl.
CPC .......... *A61G 11/003* (2013.01); *A61G 11/009* (2013.01); *A61B 5/0402* (2013.01); *A61B 5/14551* (2013.01); *A61B 2560/0242* (2013.01); *A61G 11/002* (2013.01); *A61G 11/004* (2013.01); *A61G 11/005* (2013.01); *A61G 2203/46* (2013.01)

(58) Field of Classification Search
USPC .......................................... 600/21, 22; 5/603
See application file for complete search history.

(56) References Cited

U.S. PATENT DOCUMENTS

| | | | |
|---|---|---|---|
| 4,936,824 A | 6/1990 | Koch et al. | |
| 5,149,030 A * | 9/1992 | Cockrill | 248/129 |
| 5,376,761 A | 12/1994 | Koch et al. | |
| 5,474,517 A | 12/1995 | Falk et al. | |
| 6,213,935 B1 | 4/2001 | Mackin et al. | |
| 6,409,654 B1 * | 6/2002 | McClain | 600/22 |
| 6,956,175 B1 | 10/2005 | Daly et al. | |
| 7,038,588 B2 | 5/2006 | Boone et al. | |
| 7,255,671 B2 * | 8/2007 | Boone et al. | 600/22 |
| 7,282,022 B2 | 10/2007 | Falk et al. | |
| 7,311,657 B2 | 12/2007 | Boone et al. | |
| 7,357,811 B2 | 4/2008 | Dykes et al. | |
| 7,364,539 B2 | 4/2008 | Mackin et al. | |
| 7,442,163 B2 | 10/2008 | Ten Eyck et al. | |
| 7,927,269 B2 | 4/2011 | Ten Eyck et al. | |
| 2002/0044059 A1 | 4/2002 | Reeder et al. | |
| 2002/0196141 A1 | 12/2002 | Boone et al. | |
| 2003/0200117 A1 * | 10/2003 | Manetta | G06Q 50/22 705/2 |
| 2004/0236174 A1 | 11/2004 | Boone et al. | |
| 2004/0236175 A1 | 11/2004 | Boone et al. | |
| 2009/0240098 A1 * | 9/2009 | Ten Eyck et al. | 600/22 |
| 2010/0030122 A1 * | 2/2010 | Gaspard | 601/136 |
| 2010/0261948 A1 * | 10/2010 | Chilton, III | 600/22 |
| 2011/0113555 A1 * | 5/2011 | Smith | 5/601 |

* cited by examiner

*Primary Examiner* — Charles A Marmor, II
*Assistant Examiner* — Thaddeus Cox
(74) *Attorney, Agent, or Firm* — Andrus Intellectual Property Law, LLP (57) ABSTRACT

An infant care system includes an infant care tower configured to receive at least one medical device. A processor operates the infant care tower and the at least one medical device. A bassinet is configured to receive an infant patient within a microenvironment defined and maintained by the bassinet. Upon connection of the bassinet to the infant care tower, the processor operates to control both the infant care tower and the bassinet in maintain the microenvironment of the bassinet. In a method of treating an infant patient, an infant patient is provided in a microenvironment defined and maintained by a bassinet. The bassinet is communicatively connected to the care tower and a first processor of the infant care tower operates the bassinet to maintain the microenvironment to provide medical care to the infant patient with the at least one medical device of the infant care tower.

20 Claims, 4 Drawing Sheets

SYSTEM AND METHOD OF NEONATAL CARE

BACKGROUND OF THE INVENTION

The present disclosure relates to the field of infant care. More specifically, the present disclosure relates to systems and methods of creating a neonatal care environment.

Infant patients, and particularly neonates can experience relative rapid improvement or degradation in condition. The acuteness of the patient's condition has an effect on the monitoring and therapy action taken by a care provider to address the needs of the infant patient. In general, it is preferable to move neonates as little as possible and rather to keep them maintained within a microenvironment. This can present a challenge when the acuteness of the neonates condition changes as it is often required to move the neonate to a new microenvironment in order to provide the monitoring and therapy required by the patient's condition.

Additionally, due to the stratification in the case required by neonates depending upon the acuteness of their condition, a neonatal intensive care unit (NICU) often must maintain redundant sets of equipment in order to have the capacity to treat each neonate in the NICU according to the acuteness of the infant patient's condition.

BRIEF DISCLOSURE

In accordance with an embodiment disclosed herein, an infant care system includes an infant care tower configured to receive at least one modular medical device. A processor is communicatively connected to the infant care tower and operates the infant care tower and the at least one medical device. A bassinet is configured to receive an infant patient within a microenvironment defined and maintained by the bassinet. Connection of the bassinet to the infant care tower communicatively connects the bassinet to the processor and the processor operates to control both the infant care tower and the bassinet in maintaining the microenvironment of the bassinet and the processor operates the at least one medical device of the tower to provide care to the infant patient.

In accordance with an embodiment disclosed herein, an infant care system includes a plurality of infant care towers, each of the plurality of infant care towers includes a graphical display, a user input device, at least one medical device, and a processor that operates the graphical display and user input device. A neonatal intensive care unit (NICU) computer is communicatively connected to the plurality of infant care towers and is connected to a non-transient computer readable medium such that the NICU computer operates the at least one medical component of the plurality of infant care towers. A bassinet is configured to receive an infant patient within a microenvironment defined and maintained by the bassinet. The bassinet is configured for communicative connection to any of the plurality of infant care towers. Communicative connection between the bassinet and any of the plurality of infant towers causes the processor of a connected tower to operate the bassinet to maintain the microenvironment.

In accordance with an embodiment as disclosed herein, a method of treating an infant patient includes providing an infant patient in a microenvironment defined and maintained by a bassinet configured for communicative connection. The first infant care tower is provided with a first processor and at least one medical device associated with a first level of patient condition severity. The bassinet is communicatively connected to the first infant care tower and the first processor operates the bassinet to maintain the microenvironment. Medical care is provided to the infant with the at least one medical device associated with the first level of patient acuity.

BRIEF DESCRIPTION OF THE DRAWINGS

The drawings illustrate the best mode presently contemplated of carrying out the disclosure. In the drawings.

DETAILED DISCLOSURE

Figure 1:
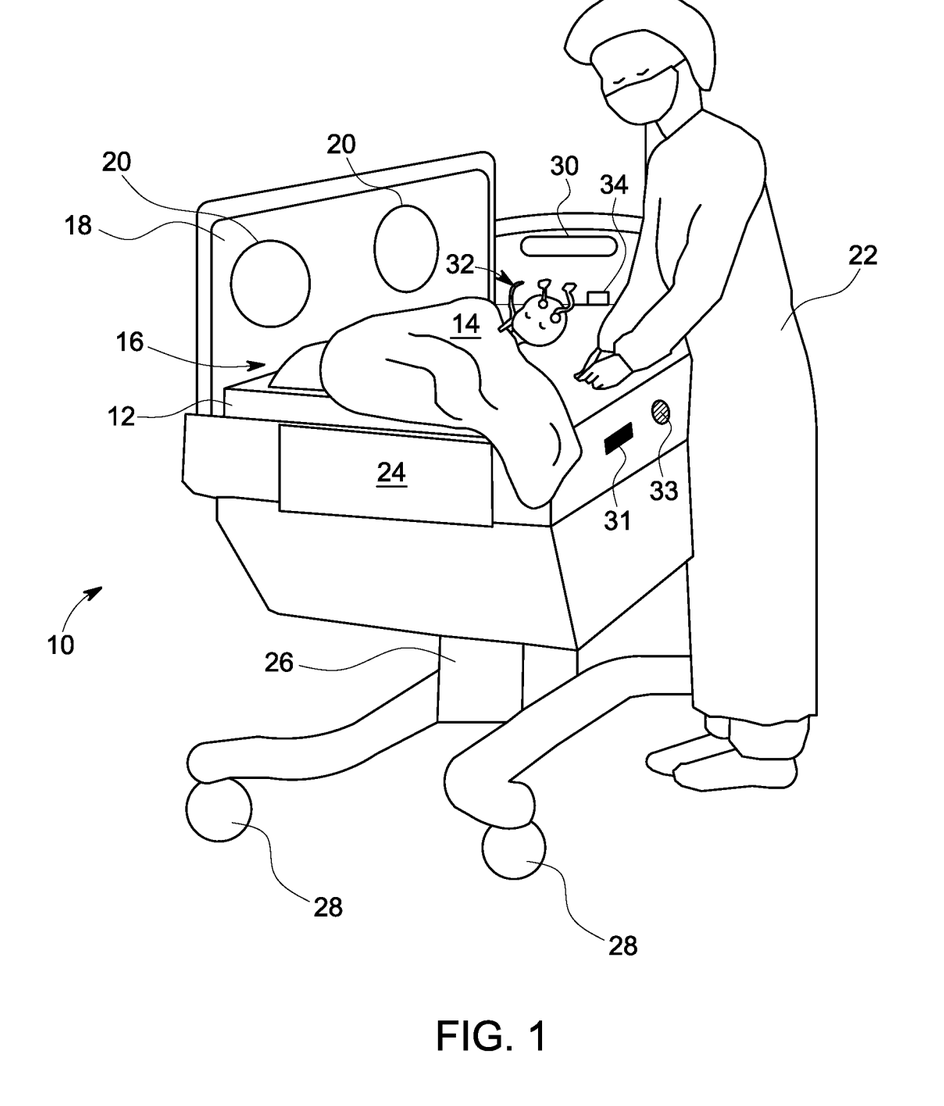
FIG. 1 is an environmental view of a bassinet in accordance with an embodiment of the infant care system as disclosed herein.

FIG. 1 is an environmental view of an embodiment of a bassinet 10. The bassinet 10 includes a generally horizontal surface 12 that supports an infant patient 14. The bassinet 10 creates a microenvironment 16 about the infant patient 14. The microenvironment 16 can include an environment that is passively or actively conditioned in the vicinity of the infant patient 14. In one embodiment, the bassinet 10 uses a wall 18, or a plurality of walls (not depicted), to create and control the microenvironment 16 about the infant patient 14. The wall 18 may be movable or otherwise adjustable to facilitate access into the microenvironment 16. In some embodiments, the bassinet 10 may include one or more arm ports 20. The wall 18 can block drafts or other air flow onto or past the infant patient 14, while preventing convective cooling of the infant patient 14 from such air flow. Arm port 20 can enable a clinician 22 to access the infant patient 14 without moving the wall 18.

Embodiments of the bassinet 10 further include a heater 24 positioned in the bassinet 10 below the horizontal surface 12. In such embodiments, the bassinet 10 operates as an incubator or a warmer. In one embodiment, the heater 24 is a convective heater that draws in ambient air, heats the ambient air exemplarily with a heating coil (not depicted) or other heating element, and blows the heated air into the microenvironment 16 through one or more vents (not depicted). Alternatively, the convective heater 24 heats the horizontal surface 12, which in turn heats the microenvironment 16 and the infant patient 14. In an alternative embodiment, the heater 24 operates as a radiant warmer, warming the horizontal surface 12 that supports the infant patient 14.

The bassinet 10 further includes an adjustable pedestal 26 that is operable to vertically adjust the horizontal surface 12. The bassinet 10 further includes casters 28. The casters 28 are configured to make the bassinet 10 mobile, such that the bassinet 10 may be moved between locations for receiving, transporting, and caring for the infant patient 14. It will be recognized by a person of ordinary skill in the art that alternatives to the casters 28 may be used in alternative embodiments within the scope of the present disclosure to make the bassinet 10 mobile.

The bassinet 10 further includes a user interface 30 that exemplarily includes a graphical display and a data input device. In one non-limiting example, the user interface 30 may integrate both the graphical display and the user input device through the use of a touch sensitive display. The user interface 30 is operated by a processor (not depicted) that executes computer readable code stored on a computer readable medium such as to operate the user interface 30 in order to present the clinician 22 with patient data or prompts for inputs by the clinician, to receive those inputs, and to execute the electronic controls and functions of the bassinet 10, including, but not limited to the operation of the heater 24 to control the microenvironment 16.

The bassinet 10 is further equipped, in some embodiments, with a physiological sensor 32. The physiological sensor 32 may be any of a variety of general patient monitoring sensors, including, but not limited to, temperature, SpO2, or electrocardiogram (ECG). It is understood that in some embodiments, due to the limited complexity of the user interface 30, the complexity or specialization of the physiological sensor 32 may be limited to be commensurate in operation with the bassinet 10. Also, the bassinet 10 may include an environmental sensor 34, which in one embodiment is a temperature sensor. The environmental sensor 34 may be positioned in any of a variety of locations in order to monitor the microenvironment 16 created by the bassinet 10. In still further embodiments, the environmental sensor 34 may also include an oxygen sensor and/or a humidity sensor to further monitor the microenvironment 16. In some embodiments, the aforementioned processor (not depicted) can use the information provided by the physiological sensor 32 in the environmental sensor 34 in conjunction with inputs received through the user interface 30 by the clinician 22 to control the microenvironment 16 exemplarily, the heater 24, or in a still further embodiment, a humidifier (not depicted).

Embodiments of the bassinet 10 may operate with energization obtained from plugging into the electrical utility supply of a medical care facility, and/or from energization from an onboard battery (not depicted). It will be recognized that embodiments of the bassinet 10 that at least optionally operate on battery energization can do so in a mobile fashion such that the infant patient can still be cared for with the bassinet even while the infant patient is in transit between locations within a medical care facility.

In an exemplary embodiment, the bassinet 10 further includes at least one auxiliary data port 31. The auxiliary data port 31 is exemplarily a USB port, or other known data connection into which additional sensors or devices can be plugged in for use by the clinician, in caring for the infant patient 14. Similarly, embodiments of the bassinet 10 may include an auxiliary gap port 33, which, as described in further detail herein, may be configured for attachment of a breathing circuit (not depicted) for the delivery of mechanical ventilation or other respiratory assistance to the infant patient 14.

However, it will be recognized that the stand alone functionality of the bassinet 10 is limited by the above-referenced processor, user interface, and integrated physiological and environmental sensors.

Figure 2:
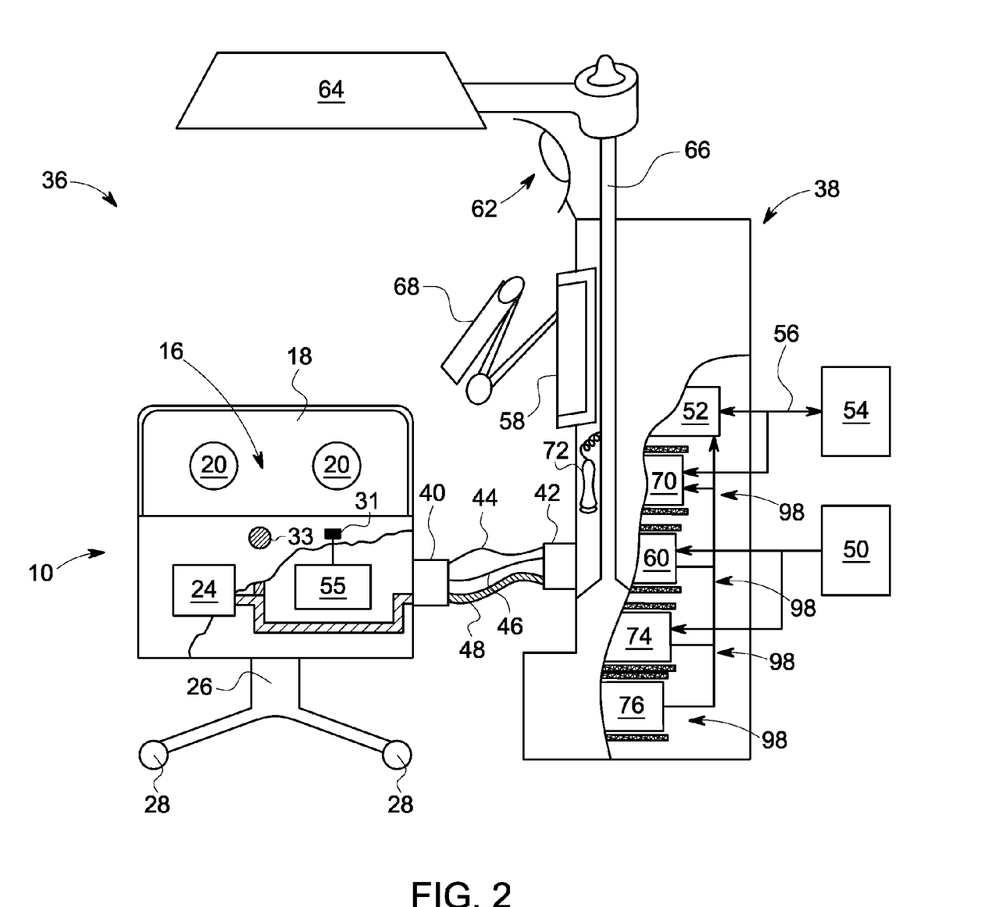
FIG. 2 is a side view of an embodiment of an infant care system.

FIG. 2 is a side view of an embodiment of an infant care system 36. The infant care system 36 generally combines the bassinet 10 with an infant care tower 38. Generally, as described in further detail herein, the infant care tower 38 is a relatively stationary structure, which may be a movable device that is kept in a generally fixed location, may be constructed in place, or may be integrated into the physical construction of the location in which it resides. On the other hand, as described above, the bassinet 10 is a generally movable device, exemplarily through the use of casters 28 in the bassinet 10. Therefore, an infant patient, once placed in the bassinet 10 can receive medical care, including monitoring, diagnostics, and therapy within the capabilities of the bassinet 10, or the bassinet 10 can be moved into connection with the infant care tower 38, such that the infant patient receives additional medical care as supported by the infant care tower 38, and as disclosed in further detail herein.

A connection interface 40 of the bassinet 10 is configured to provide various types of interconnection from the bassinet 10 to a connection interface 42 of the infant care tower 38. It is to be recognized that the connection interfaces 40 and 42, respectively may in one embodiment, include ports that receive connectors that extend from the opposite interface, or alternatively, if both of the connection interfaces 40 and 42 include such receiving ports, a separate connector can extend between each of the parts of interfaces 40 and 42. Such connectors may be configured for the particular connection to be made, in non-limiting examples, such connections can include an electrical/power connection 44, data connection 46, and gas connection 48, each of which will be discussed in further detail herein.

The connection between the bassinet 10 and the infant care tower 38 functionally integrates the bassinet 10 with the infant care tower 38 such that the monitoring, diagnostic, and therapy capabilities of the bassinet 10 are supplemented and enhanced by the infant care tower 38. The power connection 44 between the bassinet 10 and the infant care tower 38 enables the bassinet 10 to operate using the utility electricity services of the medical care facility, rather than operating on battery power, as referenced above. In addition, the power connection 44 can serve to charge the battery of the bassinet 10, such that the bassinet 10 can operate when the infant patient is moved between infant care towers 38, as described herein, or between locations in a medical care facility.

The data connection 46 between the bassinet 10 and the infant care tower 38 enables the transfer of monitored data from the integrated sensors of the bassinet 10, as described above, including, but not limited to, the physiological sensor 32 and the environmental sensor 34. Additionally, the data connection 46 can transfer data acquired by any additional medical devices, including those disclosed herein, connected to the auxiliary data port of the bassinet 10. As described herein in further detail, the infant care tower 38 can use these monitored data to provide medical care to the infant patient beyond that which is available through the use of the bassinet 10. Also, the data connection 46 enables the transfer of data from the infant care tower 38 to the bassinet 10, namely to the processor of the bassinet 10 such as to operate the processor of the bassinet 10 in a manner to operate components such as the heater 24 or user interface 30 to provide monitoring, diagnostic, or therapeutic care to the infant patient as directed by the infant care tower 38.

Gas connection 48 provides a supply of medical gas from the infant care tower 38 to the bassinet 10. While generally referenced as medical gas, such medical gas can refer to a variety of gases or gas mixtures. Such medical gases may include air, oxygen, nitrogen, and nitrous oxide; however, a person of ordinary skill in the art will recognize that a medical gas provided to the bassinet 10 with gas connection 48 may include alternative gases, or a combination of one or more of the gases identified above. The medical gas provided to the bassinet 10 by the infant care tower 38 can be used by the bassinet 10 to condition the microenvironment 16, or to provide mechanical ventilation, as described herein.

The medical gas directed to the bassinet by gas connection 48 from the infant care tower 38 can be provided to the infant care tower 38 from a gas source such as a gas cylinder (not depicted) stored within the infant care tower 38, or a centralized medical gas supply 50 such as is built into the medical care facility and to which the infant care tower 38 is fluidly connected.

The infant care tower 38 includes a processor 52 which may be any of a variety of computer processing units, controllers, or microcontrollers, as recognized by a person of ordinary skill. The processor 52 is communicatively connected to a network 54 of the medical care facility through the communicative connection 56 with the network 54, the processor 52 has access to data and instructions as provided through the network 54. This can include access to an electronic medical record (EMR) server (not depicted) upon which information regarding the infant patient in the bassinet 10 can be accessed or stored. Communication between the EMR server and the processor 52 can be bi-directional such that the processor 52 can cause data to be stored in the EMR of the infant patient, and alternately the processor 52 can retrieve data from the infant patient's EMR for use in providing medical care disclosed herein. Additionally, the processor 52 may receive remote instructions and/or software updates from remotely located users through the network 54.

The processor 52, through the data connection 46 is communicatively connected to the bassinet 10, and namely a processor 55 of the bassinet 10. By communicatively connecting the processor 52 with the processor 55, the processor 52 of the infant care tower 38 can operate the functions of the bassinet 10 controlled by the processor 55 when the bassinet 10 is operating independently. Additionally, through the data connection 46 and the communicative connection 56, the processor 55 can push recorded physiological and environmental data to the network 54, exemplarily for storage in the infant patient's EMR. In embodiments, this transfer is facilitated by the processor 52 which may intermediately receive the pushed data and selectively process and transmit the data to the network 54 for storage in the EMR.

The infant care tower 38 includes a user interface 58 that includes both a graphical display for the visual presentation of data related to the infant patient and/or the devices of the infant care tower 38 or bassinet 10. Additionally, the user interface 58 can present prompts to a clinician for actions or data inputs which the user interface 58 can further receive. In some embodiments, the user interface 58 includes a flat screen display in conjunction with a keyboard for data entry. In an alternative embodiment, the user interface 58 is a touch-sensitive graphical display that combines the display and data entry functions of the user interface 58.

In an embodiment of the infant care system 36 wherein the bassinet 10 is connected to the infant care tower 38 by at least a data connection 46, the processor 52 of the infant care tower can override the operation of the user interface 30 of the bassinet and the user interface 58 can instead operate to present data and receive inputs for the combined infant care system 36. In this embodiment, a user interface 58 is larger and more robust in data presentation and input capability in comparison to the user interface 30 of the bassinet 10. In such an embodiment, the user interface 58 can present the data obtained from the physiological sensor 32 and environmental sensor 34, while also receiving a wider variety of inputs and information from the other medical devices of the infant care tower 38, disclosed herein. In one such embodiment, the processor 52 is connected to a computer readable medium programmed with computer readable code, such that processor 52 can operate the user interface 58. The processor 52 is further connected to communicative connection 56 in order for the clinician to access, receive, and edit data from the EMR of the infant patient. In such an embodiment, the infant care tower 38 can facilitate the charting of observed and monitored conditions of the infant patient by the clinician at the bassinet bedside, rather than recording notations for later data entry at a different EMR accessible terminal (not depicted).

The infant care tower 38 further includes at least one modular device that works in conjunction with the bassinet 10 when the bassinet 10 is connected to the infant care tower 38 in order to provide enhanced monitoring, diagnostic, or therapeutic functions for caring for the infant patient in the bassinet 10.

Embodiments of the infant care tower 38 may include one or more modular devices for controlling the microenvironment 16 of the bassinet 10. As noted above, the bassinet 10 may include its own heater 24, however, the heater 24 of the bassinet 10 may be limited in its ability to modify the microenvironment 16. Therefore, environments of the infant care tower 38, through the processor 52 may operate the heater 24 in a manner such as to provide more or more sophisticated heat therapy to the infant patient and provide improved control over the environmental conditions of the microenvironment 16. In such embodiment, the additional energy provided through a power connection 44 may allow the processor 52 to operate the heater 24 either hotter or more efficiently in order to provide more heat to the microenvironment 16. Alternatively, the processor 52 may be programmed with more sophisticated heating algorithms that take into account data received across the data connection 46 from the physiological sensor 32 or environmental sensor 34. Furthermore, the infant care tower 38 may include a gas delivery device 60 that receives the medical gas from the medical gas supply 50, and in an embodiment receives more than one medical gas from the medical gas supply 50 and provides a mixture of medical gases through the gas connection 48 to the bassinet 10. In an embodiment the medical gas provided to the bassinet 10 can be heated by the heater 24 of the bassinet under the control of the processor 52 and delivered to the microenvironment 16 for improved provision of microenvironment temperature and atmosphere composition (e.g. oxygen concentration).

In still further embodiments, the infant care tower 38 may include a radiant heater 62 that is operable by the processor 52 to provide further warming therapy to control the temperature of the microenvironment 16 about the infant patient. The radiant warmer 62 can be used in embodiments in conjunction with the convective heater 24 under the operation of the processor 52 as the radiant warmer 62 can be complimentary in its ability to direct radiant heat energy at the infant patient, while the convective heater 24 provides a generally warmed microenvironment 16.

Embodiments of the infant care tower 38 may further include a canopy 64 connected to a lifting mechanism (not depicted) that raises and lowers the canopy 64 relative to the bassinet 10. In one embodiment, the canopy 64 is movably secured to the infant care tower 38 by a rail 66 of the infant care tower 38 along which the canopy 64 moves. It will be recognized by one of ordinary skill that alternative constructions, including, but not limited to servo motors or rack and pinion embodiments may be used in alternative lifting mechanisms rather than the rail 66 to move the canopy 64 with respect to the bassinet 10, and such embodiments are considered within the current disclosure.

When the canopy 64 is lowered to be used in conjunction with the bassinet 10, the bassinet 10 can be functionally used as a hybrid incubator, such as the OmniBed available from GE Healthcare. The canopy 64 may include additional components, such as a radiant warmer, lights, or additional sensors of patient or environmental conditions. In a still further embodiment, the canopy 64 may include a phototherapy device, or alternatively, the phototherapy device 68 can be a device connected to the infant care tower. The phototherapy device 68 may exemplarily be the Lullaby™ or the BilliBlanket® phototherapy devices, both available from GE Healthcare.

Embodiments of the infant care tower 38 can include a picture archiving and communication system (PACS) 70 that is in communicative connection with the network 54 and the processor 52 in an embodiment, the PACS can be integrated into the software operated by the processor 52, or may be an additional processing component to handle the imaging data. The PACS 70 enables the processor 52 to present recorded diagnostic images of the infant patient as available through the network 54 on the user interface 58. Additionally, the PACS 70 may be used in conjunction with one or more imaging devices incorporated into an embodiment of the infant care tower 38. One such embodiment includes an ultrasound doppler transducer 72 that can be used by a clinician in acquiring acoustical images of portions of the infant patient. While ultrasound transducer 72 is depicted as imaging device, it is to be recognized that alternative embodiments of the infant care tower 38 and PACS 70 may use an alternative patient imaging platform, exemplarily X-ray, which may be incorporated as a separate device in the infant care tower 38, or may be integrated into the canopy 64.

A still further embodiment of the infant care tower 38 includes a mechanical ventilation device 74 that is fluidly connected to the medical gas supply 50 and is communicatively connected to the processor 52. The mechanical ventilator 74 can include a breathing circuit (not depicted) that extends from the infant care tower 38 to provide the mechanical ventilation to the infant patient. In an alternative embodiment, the breathing circuit is connected to the auxiliary gas port 33 of the bassinet 10, the gas port 33 being connected to the gas connection 48. The breathing circuit then extends from the gas port 33 to the infant patient. In this embodiment, the mechanical ventilator 74 operates to deliver the respiratory support to the infant patient by controlling the delivery of medical gas through the gas connection 48 between the infant care tower 38 and the bassinet 10. The mechanical ventilator 74 has the functionality to provide complex forms of respirator support, including, but not limited to, continuous positive airway pressure (CPAP) ventilation.

Embodiments of the infant care tower 38 further include a physiological monitoring device 76 that operates in addition to or enhances the physiological monitoring provided on the bassinet 10. In one embodiment, the physiological monitoring device 76 includes transducers (not depicted) that extend from the infant care tower 38 to be connected to the infant patient. In an alternative embodiment, the physiological monitoring device 76 connects to the bassinet 10 through the data connection 46 and leverages the physiological sensor 32 of the bassinet for physiological monitoring of the infant patient. In addition, additional monitoring devices can be connected to the at least one auxiliary data connection 31 of the bassinet, exemplarily a USB port, in order to connect physiological transducers that are beyond the scope of the physiological monitoring capability of the bassinet, but which physiological monitoring capability is functionally provided by the physiological monitoring device 76. Such examples may include ECG or pulse oximetry, if not provided by the physiological sensors 32 of the bassinet 10, electroencephalograph (EEG), non-invasive blood pressure (NIBP), and others as recognized by one of ordinary skill in the art. In addition to the functionality of physiological signal acquisition, the physiological monitoring device 76 further provides the signal processing and data analysis to provide more advanced physiological monitoring capability and analysis. As a non-limiting example, while embodiments of the bassinet 10 may monitor ECG to determine the heart rate of the infant patient, the physiological monitoring device 76 can include algorithms and processing capability to provide further analysis of the ECG exemplarily, but not limited to arrhythmia detection and other cardiac health risk assessments.

Figure 3:
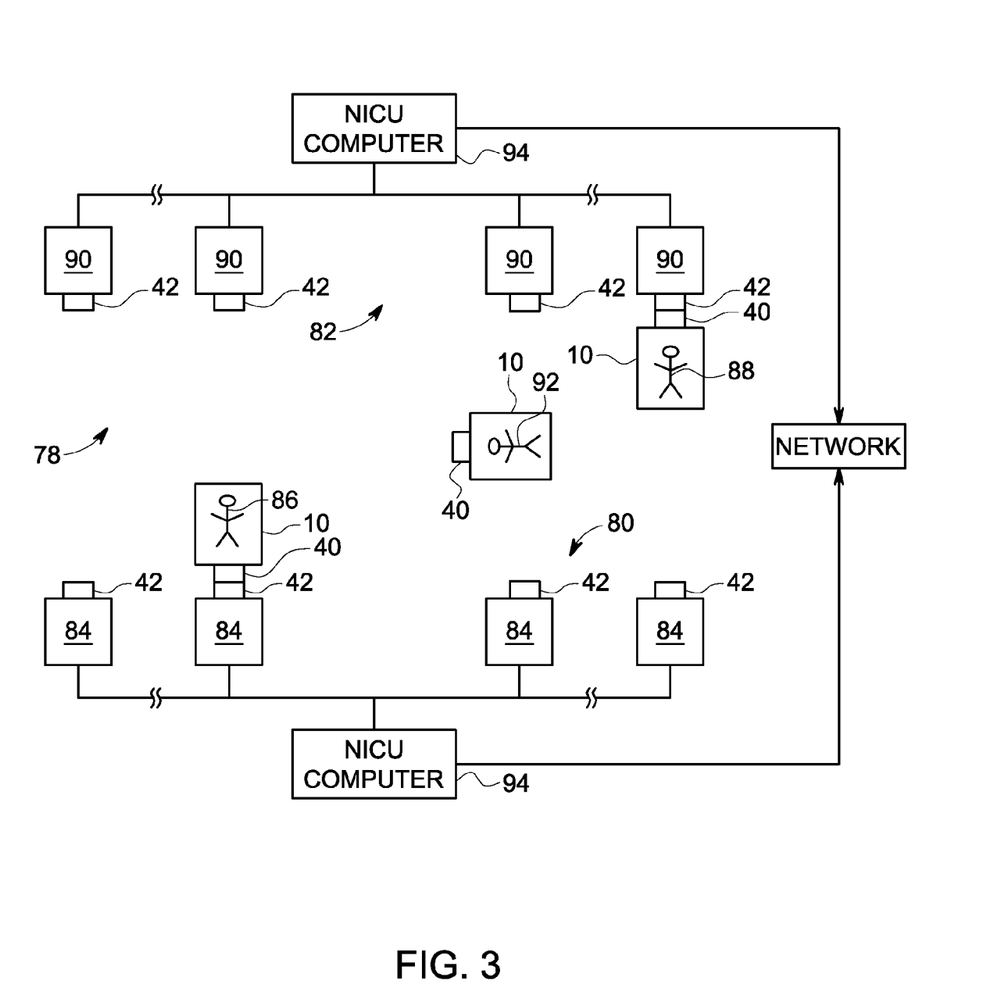
FIG. 3 is a system diagram in accordance with an embodiment of the infant care system.

FIG. 3 is a system diagram and embodiment of an NICU 78 of a medical care facility. The layout and organization of the NICU 78 as depicted in FIG. 3 is intended to be merely exemplarily and is not intended to be limiting in any way as to the organization, layout, or use of embodiments disclosed herein within a medical care facility.

The system diagram of FIG. 3 includes two groups or pods of infant care towers. As will be described in further detail herein the two pods of infant care towers are configured to treat infant patients of varying acuteness of condition. In the embodiment of the NICU 78 depicted in FIG. 3, one pod is organized as a high severity condition pod 80 and the other pod is organized as a medium severity condition pod 82. Therefore, the bassinet 10 of the most critical risk infant patient 86 exemplarily, an extremely low birth weight (ELBW) patient, is connected to a high severity infant care tower 84, while a bassinet 10 of an infant patient deemed to be a medium risk infant patient 88, exemplarily a neonate, is connected to a medium severity infant care tower 90 of the medium severity condition pod 82. Furthermore, a low risk infant patient 92, exemplarily, a full term infant, can be cared for in the bassinet 10 as a stand-alone device, as described above.

It is to be understood that the risk evaluation and analysis of the infant patients as depicted within FIG. 3 are intended to be merely exemplarily and each medical care facility may have its own procedures and protocols in determining the risk and appropriate level of care to be provided to each individual infant patient. The embodiment of the NICU 78 as depicted in accordance with an embodiment as disclosed herein as merely exemplarily of the disclosed feature that the NICU 78 may be arranged in pods 80 and 82 of infant care towers 84 and 90, respectively, configured for treating infant patients of varying risk levels.

The high severity infant care tower 84 is exemplarily configured with many or all of the features as described in the embodiment of the infant care tower 38 depicted in FIG. 2. In such an embodiment, the canopy 64 can be lowered over the bassinet 10 to create a hybrid incubator for controlling the microenvironment 16 about the critical risk infant patient 86. As the critical risk infant patient 86 is in most need of monitoring, diagnosis, and therapy, the high severity infant care tower 84 is outfitted with most or all of the medical devices described with respect to FIG. 2 to place these devices at the fingertip of a clinician for prompt treatment of the critical risk infant patient 86, without having to move the critical risk infant patient 86 to another location, or even another bassinet 10.

As noted above, the infant care towers are generally configured to modularly receive medical devices or components, such that the infant care towers can be configured with the tools necessary for the monitoring, diagnostics, and treatment of infant patients of varying severities of condition. In one embodiment of the infant care tower 38, as depicted in FIG. 2, the infant care tower 38 includes a plurality of racks or bays 98 configured to receive one or more modular medical devices. In some embodiments, the rack or bays 98 are generically designed to receive any of a plurality of modular medical devices, while in other embodiments, a separate rack or bay 98 is configured to receive a specific modular medical device.

The medium severity infant care tower 90 may be equipped with a reduced set of medical devices, including only those medical devices that would be needed to treat an infant patient with a medium severity of condition. As a non-limiting example, such a medium risk configuration may include medical devices such as the phototherapy device, physiological monitoring device, and the radiant warmer, while eliminating medical devices such as the canopy and the mechanical ventilator. It is also to be noted that from the standpoint of the medical care facility, many of the medical devices needed to treat the most critical of infant patients, are also generally more expensive, and therefore, the medium severity infant care tower 90 can be outfitted at an appropriate level of care at a reduced cost as compared to the high severity infant care towers 84.

In a still further aspect of the system depicted in FIG. 3, in the event that more high severity infant care towers 84 are needed than are available in the high severity condition pod 80, a medium severity infant care tower 90 can be converted to a high severity infant care tower 84 by the addition of further medical devices in order to arrive at the care capability needed to treat the additional critical risk infant patient.

The respective towers 84, 90 of both of the pods 80, 82 are communicatively connected to one or more NICU computers 94. The NICU computer 94 comprises a processor and non-transient computer readable media programmed with computer readable code such that the NICU computer 94 operates in conjunction with the processor of each of the infant care towers 84 and 90. Similar to the manner in which the processor of the infant care towers supplements and enhances the functionality provided by the processor of the bassinet, in an embodiment, the NICU computer provides more complex signal processing, analysis, and software than is available individually at the processor of each of the infant care towers. Particularly for high demand signal processing and/or data analysis requirements, such as may be needed for PACS, ultrasound, or digital X-ray functionality of the infant care tower, the NICU computer 94 can work with these modular medical devices of the respective infant care towers such that the respective processors of the tower may not be overburdened by these additional computing demands. Also, these relatively complex functions, particularly imaging, although not necessary limited to imaging functionalities, are generally only intermittently used and therefore such operational software and processing need not be generally available in parallel among infant care towers within a single pod. Rather, the medical care facility can efficiently provide this functionality to each of the infant care towers in a pod while the software resides on the NICU computer 94, rather than at each of the individual towers. This can help to reduce the cost of an individual infant care tower unit, particularly with medical devices wherein the transducers or other electrical non-processing hardware components of the devices only account for a percentage of the cost associated with such a device in comparison to the software and processing functions needed for such functionality.

The NICU computer 94 is communicatively connected to the network 96 of the medical care facility, such that, through the NICU computer 94 each of the infant care towers have access to medical data, exemplarily the EMR of the infant patient. Therefore, as described above, the infant care towers can be used, through the NICU computer 94, to perform charting functions and updates to the infant patients EMR while the clinician is at the infant patient's bedside. In a still further feature, a low risk infant patient 92 being cared for in a bassinet 10 operating independent from any infant care tower can be transported in the bassinet 10 to be communicatively connected to an infant care tower 84 and 90, that is currently unused to provide care to another infant patient such that the data connection capabilities provided between the respective connection interfaces 40 and 42 of the tower and the bassinet for routine checkup, physiological monitoring, and chart updating functionalities without having to move even the low risk infant patient 92 out of the microenvironment provided by the bassinet 10.

Figure 4:
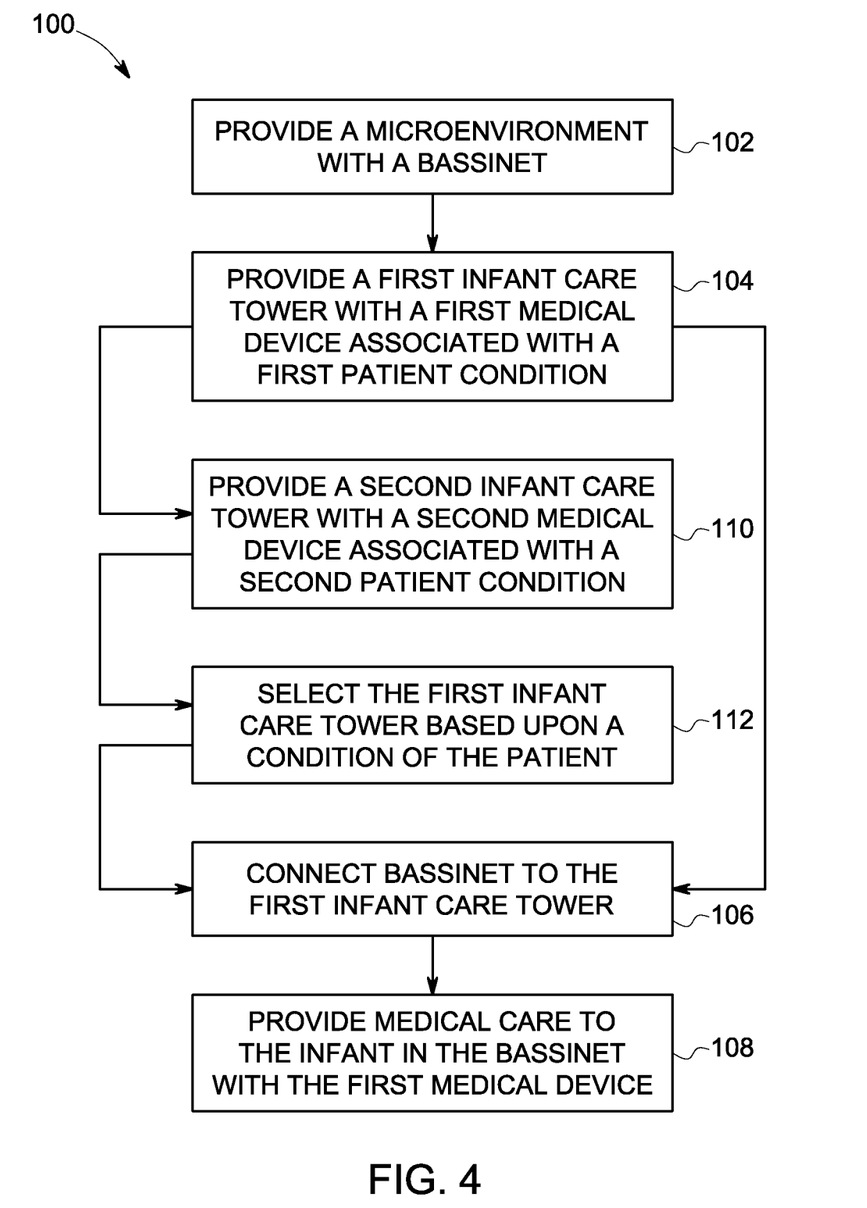
FIG. 4 is a flow chart in accordance with an embodiment of a method of treating an infant patient.

FIG. 4 is a flow chart that depicts an embodiment of a method 100 of treating an infant patient. The method 100 starts with providing a microenvironment with a bassinet at 102. As disclosed above, the microenvironment can be conditioned by the bassinet by controlling the heating, illumination, and/or humidity about an infant patient.

Next at 104 a first infant care tower is provided with a first medical device associated with a first patient condition. In one such embodiment, the infant care tower is configured with a plurality of medical devices to create an infant care tower configured to treat an infant patient of a particular identified condition or risk level. In one exemplarily embodiment, the infant care tower is configured to provide care to an ELBW patient, or other high-risk infant patient, while in alternative embodiments, the infant care tower is configured to treat an infant patient with a lower risk.

In one embodiment of the method, the bassinet with the infant patient is connected to the first infant care tower at 106. The connection between the bassinet and the first infant care tower, may be a communicative connection that is made either with a wired or a wireless data connection, in addition, the bassinet may be connected to the first infant care tower such that the first infant care tower provides a supply of medical gas or electrical power to the bassinet. Through the connection of the bassinet to the first infant care tower at 106, medical care is provided to the infant in the bassinet with at least the first medical device at 108. The connection of the bassinet to the first infant care tower provides communication between the infant care tower and the bassinet, such that the infant care tower enhances and facilitates the care of the infant patient within the bassinet by operating the bassinet to control the microenvironment provided by the bassinet, while in addition providing additional care functionality through the at least one medical device of the infant care tower.

In an alternative embodiment of the method 100 in accordance with the present disclosure, a second medical care tower is provided with a second medical device associated with a second patient condition at 110. In this embodiment, the first infant care tower and the second infant care tower are each configured with at least one medical device in order to provide a first infant care tower and a second infant care tower that are configured differently to provide care to infant patients but exhibiting different levels of need or physiological condition. In such an embodiment, one of the infant care towers is configured to provide care to high risk infant patients while another infant care tower is configured to provide care to a low risk infant patient. In such an embodiment at 112, the first infant care tower is selected based upon the condition of the patient. The infant patient's medical condition is used to determine the medical care functionality needed for that infant patient and an infant care tower is selected to provide those care functions, exemplarily the first infant care tower and the bassinet with the infant patient is connected to the first infant care tower at 106. In such an alternative embodiment, at 108 if the condition of the infant patient changes such that the medical care needed by the infant patient would be more appropriately provided by the second infant care tower, the bassinet can be disconnected from the first infant care tower and reconnected to the second infant care tower such that medical care can be provided to the infant in the bassinet with the second medical device.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An infant care system, comprising:
   an infant care tower, comprising a first rack, and a second rack, a graphical display, a user interface, and a tower interface;
   a first medical device removably received within the first rack;
   a second medical device removably received within the second rack;
   a processor communicatively connected to and configured to operate the infant care tower, graphical display, user interface, first medical device and second medical device;
   at least one connector connected at a first end to the tower interface;
   a neonatal intensive care unit (NICU) computer communicatively connected to the processor of the infant care tower and connected to a non-transient computer readable medium, such that the NICU computer operates the first medical device and the second medical device through the processor of the infant care tower; and
   a bassinet configured to receive an infant patient within a microenvironment defined and maintained by the bassinet, the bassinet further physically connected to at least one of the first medical device and the second medical device through the infant care tower by a removable connection of a bassinet interface to the at least one connector and communicatively connected to the processor through the infant care tower by removable connection of the bassinet interface to the at least one connector;
   wherein the processor operates to control both the infant care tower and the bassinet in maintaining the microenvironment of the bassinet, and the processor operates the first and second medical devices of the tower to provide care to the infant patient.

2. The infant care system of claim 1, wherein the first medical device is a mechanical ventilator, the infant care system further comprises a source of medical gas fluidly connected to the infant care tower, and the connection of the bassinet to the infant care tower fluidly connects the bassinet to the mechanical ventilator, such that the bassinet and tower are operable to provide mechanical ventilation of the infant patient in the microenvironment.

3. The infant care system of claim 2, further comprising a patient connection fluidly connected to an auxiliary gas port of the bassinet wherein the bassinet receives the medical gas from the mechanical ventilator of the infant care tower through a gas connection of the at least one connector and the bassinet provides the medical gas to the patient connection through the auxiliary gas port.

4. The infant care system of claim 1, further comprising a radiant warmer connected to the infant care tower that is operated by the processor to warm the microenvironment when the bassinet is connected to the infant care tower.

5. The infant care system of claim 1, wherein the bassinet further comprises a bassinet processor that operates the bassinet to maintain the microenvironment.

6. The infant care system of claim 5, wherein the processor is a tower processor and the tower processor operates the bassinet processor when the bassinet is connected to the infant care tower.

7. The infant care system of claim 6 wherein the bassinet further comprises at least one sensor that collects data and the bassinet processor transmits the data to the tower processor which uses the data to operate the first medical device to provide care to the infant patient.

8. The infant care system of claim 7 wherein the first medical device is a physiological data monitor, and the physiological data monitor receives physiological data from the at least one sensor and processes the physiological data for presentation by the infant care tower.

9. The infant care system of claim 7 wherein the at least one sensor is an environmental sensor that obtains environmental data regarding the microenvironment and the environmental data is provided to the tower processor when the bassinet is connected to the infant care tower.

10. The infant care system of claim 9 wherein the first medical device is a gas delivery device connected to a medical gas source and to the bassinet by a fluid connection through the at least one connector and the gas delivery device provides medical gas to the bassinet based upon the environmental data.

11. The infant care system of claim 5, wherein the bassinet comprises a convective heater communicatively connected to the bassinet processor and the bassinet processor operates the convective heater to maintain a temperature of the microenvironment.

12. An infant care system, comprising:
   a plurality of infant care towers, each of the plurality of infant care towers comprising a graphical display, a user input device, a plurality of racks, at least one medical device removably received within a rack of the plurality of racks, a processor communicatively connected to the at least one medical device and that operates the graphical display, the at least one medical device, and user input device, and a tower interface;
   at least one connector connected at a first end to the tower interface;
   a neonatal intensive care unit (NICU) computer communicatively connected to the plurality of infant care towers and connected to a non-transient computer readable medium, such that the NICU computer operates the at least one medical device of the plurality of infant care towers; and
   a bassinet configured to receive an infant patient within a microenvironment defined and maintained by the bassinet, the bassinet comprising a bassinet interface connected to a second end of the at least one connector for removable connection of the bassinet to an infant care tower of the plurality of infant care towers, the bassinet being physically and communicatively connectable to each of the plurality of infant care towers, wherein communicative connection between the bassinet and any of the plurality of infant care towers causes the processor of a connected tower to operate the bassinet to maintain the microenvironment;

wherein in a first infant care tower of the plurality of infant care towers, the at least one medical device comprises a first medical device, and in a second infant care tower of the plurality of infant care towers, the at least one medical device comprises a second medical device, the first medical device being different from the second medical device, and when the bassinet is communicatively connected to a tower of the plurality, that tower operates the at least one medical device of that tower in conjunction with the bassinet.

13. The infant care system of claim 12, wherein the bassinet comprises a convective warmer and the infant care tower comprises a radiant warmer, when the bassinet is communicatively connected to the infant care tower, the tower processor operates the convective warmer and the radiant warmer to maintain the microenvironment of the bassinet.

14. The infant care system of claim 12 further comprising an imaging device removably secured to at least one of the plurality of infant care towers, the imaging device being operated by the NICU computer through the tower processor.

15. The infant care system of claim 12, further comprising an electronic medical record (EMR) of the infant patient accessible through a network communicatively connected to the NICU computer, wherein the tower processor operates to send and receive patient data to and from the EMR of the infant patient through the NICU computer and the network.

16. The infant care system of claim 12, wherein the first medical device is a mechanical ventilator, the mechanical ventilator operable by the processor of the first infant care tower to provide medical gas to the infant patient;

wherein the at least one connector between the tower interface and the bassinet interface comprises a pneumatic connection to provide the medical gas from the mechanical ventilator to the bassinet; and wherein the bassinet comprises a patient connection fluidly connected to an auxiliary gas port of the bassinet, and the bassinet receives the medical gas from the mechanical ventilator and provides the medical gas to the patient connection through the auxiliary gas port.

17. A method of treating an infant patient, the method comprising:

providing an infant patient in a microenvironment defined and maintained by a bassinet configured for communicative connection;

providing a first infant care tower with a processor, a first plurality of racks with a bassinet interface, and a first tower interface;

removably receiving a first medical device associated with a first level of patient condition severity in a rack of the first plurality of racks;

communicatively connecting the first medical device to the processor of the first infant care tower;

providing a second infant care tower with a processor, a second plurality of racks and a second tower interface;

removably receiving a second medical device associated with the first level of patient condition severity in a rack of the second plurality of racks;

removably receiving a third medical device associated with a second level of patient condition severity in another rack of the second plurality of racks;

communicatively connecting the second medical device and the third medical device to the processor of the second infant care tower;

selecting a selected infant care tower from between the first infant care tower and the second infant care tower based upon the infant having at least one of the first level of patient condition severity and the second level of patient condition severity;

physically and communicatively connecting the bassinet to the selected infant care tower with at least one connector between the tower interface of the selected infant care tower and the bassinet interface, wherein the processor of the selected infant care tower operates the bassinet to maintain the microenvironment; and providing medical care to the infant patient in the bassinet with the selected infant care tower.

18. The method of claim 17, wherein the bassinet comprises a bassinet processor, further comprising:

communicatively connecting the bassinet processor to the processor of the selected infant care tower with the at least one connector;

operating the bassinet processor with the processor of the selected infant care tower to maintain the microenvironment.

19. The method of claim 18, wherein the bassinet comprises at least one sensor operated by the second processor to collect data, further comprising:

providing the collected data from the bassinet processor to the processor of the selected infant care tower through the at least one connector;

using the collected data with the processor of the selected infant care tower to maintain the microenvironment.

20. The method of claim 18, wherein the third medical device is a mechanical ventilator, and comprising:

providing medical gas to the bassinet through the at least one connector to provide respiratory support to the infant patient.

* * * * *